United States Patent
Pederson et al.

(10) Patent No.: US 10,888,331 B2
(45) Date of Patent: Jan. 12, 2021

(54) ACTIVE RELEASE OF EMBOLIC COILS

(71) Applicant: Boston Scientific Scimed, Inc., Maple Grove, MN (US)

(72) Inventors: Gary Pederson, Albertville, MN (US); Katherine Routh, Coon Rapids, MN (US); Ken Zhang, Maple Grove, MN (US); Jeffry Johnson, Crystal, MN (US); Devon Arnholt, Shoreview, MN (US); Joel Eggert, Plymouth, MN (US); James Rohl, Prescott, WI (US); Douglas Pagoria, Forest Lake, MN (US); John-Allen O'Brien, Drimoleague (IE); Frank Ryan, Frankfield (IE); Conor O'Sullivan, County Cork (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 104 days.

(21) Appl. No.: 15/019,574

(22) Filed: Feb. 9, 2016

(65) Prior Publication Data

US 2016/0228125 A1     Aug. 11, 2016

Related U.S. Application Data

(60) Provisional application No. 62/114,492, filed on Feb. 10, 2015.

(51) Int. Cl.
*A61B 17/12* (2006.01)

(52) U.S. Cl.
CPC .... *A61B 17/12109* (2013.01); *A61B 17/1214* (2013.01); *A61B 17/12022* (2013.01);
(Continued)

(58) Field of Classification Search
CPC ........ A61B 17/12022; A61B 17/12109; A61B 17/1214; A61B 2017/1205; A61B 2017/12054
See application file for complete search history.

(56) References Cited

U.S. PATENT DOCUMENTS 7,691,124 B2 * 4/2010 Balgobin ........... A61B 17/0057
                                                     606/191
7,942,894 B2 * 5/2011 West ................ A61B 17/12022
                                                     294/99.1
(Continued)

FOREIGN PATENT DOCUMENTS

| EP | 1260184 A1 | 11/2002 |
| EP | 2777542 A2 | 9/2014 |
| WO | 92021400 A1 | 12/1992 |

OTHER PUBLICATIONS

International Search Report and Written Opinion (dated Apr. 21, 2016), for PCT/US2016/017138 (8 pages).

*Primary Examiner* — Martin T Ton
(74) *Attorney, Agent, or Firm* — Kacvinsky Daisak Bluni PLLC

(57) ABSTRACT

The present disclosure relates to the field of embolic coils. More specifically, the present disclosure relates to systems and methods for actively releasing an embolic coil from a delivery device into a body lumen of a patient. Delivery systems of the present disclosure may allow an embolic coil to be advanced external to the distal end of a delivery catheter without being automatically released, thereby allowing the embolic coil to be repositioned prior to deployment.

20 Claims, 10 Drawing Sheets

Figure 1A:
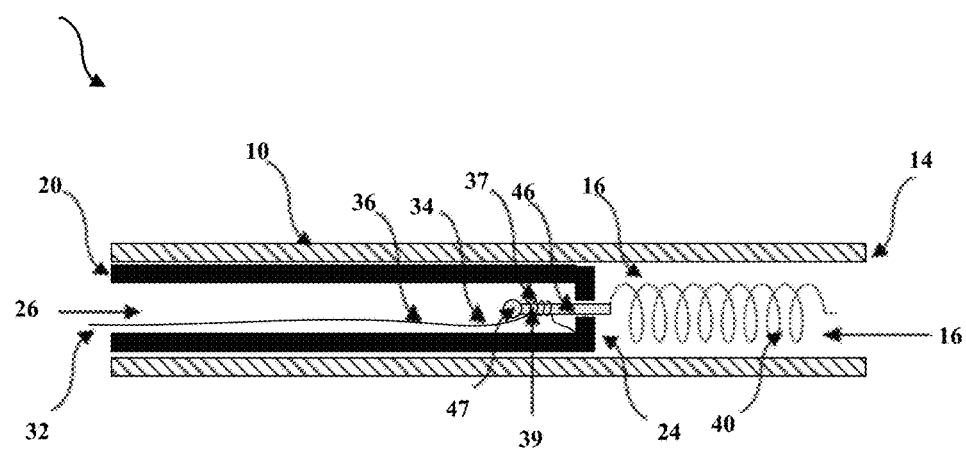

(52) U.S. Cl.
CPC ............... *A61B 2017/1205* (2013.01); *A61B 2017/12054* (2013.01)

(56) References Cited

U.S. PATENT DOCUMENTS

| | | |
|---|---|---|
| 2006/0025802 A1 | 2/2006 | Sowers |
| 2006/0276825 A1 | 12/2006 | Mitelberg et al. |
| 2007/0203519 A1 | 8/2007 | Lorenzo et al. |
| 2008/0119887 A1 | 5/2008 | Que et al. |
| 2008/0306503 A1 | 12/2008 | Que et al. |
| 2009/0036877 A1* | 2/2009 | Nardone .......... A61B 17/12022 606/1 |
| 2010/0094395 A1 | 4/2010 | Kellett |
| 2011/0060360 A1 | 3/2011 | Mitelberg et al. |
| 2012/0172913 A1 | 7/2012 | Kurrus et al. |
| 2014/0207175 A1* | 7/2014 | Aggerholm ............... A61F 2/01 606/200 |
| 2014/0236127 A1* | 8/2014 | Lee ....................... A61B 17/12 604/535 |

* cited by examiner

500

ACTIVE RELEASE OF EMBOLIC COILS

CROSS-REFERENCE TO RELATED APPLICATIONS

This application claims the benefit of U.S. Provisional Application No. 62/114,492, entitled "ACTIVE RELEASE OF EMBOLIC COILS" and filed Feb. 10, 2015, which is hereby incorporated by reference in its entirety.

FIELD

The present disclosure relates to the field of embolic coils. More particularly, the present disclosure relates to devices and methods for actively releasing embolic coils from a delivery device into a body lumen of a patient.

BACKGROUND

Various medical conditions require partial or complete occlusion of blood vessels or vascular malformations. Embolic coils (i.e., vaso-occlusive coils) have proven popular for such applications owing to their ability to be placed at such sites using a variety of percutaneous delivery techniques.

Accurate delivery of the embolic coil to the appropriate site within a body lumen is important to proper function and favorable patient prognosis. A variety of negative medical outcomes may result from the incomplete or partial occlusion of a vascular malformation, as well as unintended occlusion of nearby vasculature. Although proper placement within the patient is of great importance, many current systems are incapable of controlling embolic coil release/detachment after the embolic coil has exited the delivery catheter. The automatic release associated with many current delivery systems prevents the user from accurately positioning the embolic coil prior to detachment, and, if necessary, retracting the embolic coil into the delivery catheter. Accordingly, there is a need for delivery systems that allow the embolic coil to be advanced external to the distal end of catheter without being automatically released, thereby allowing the user to actively release the embolic coil once properly positioned, or retract the embolic coil back into the catheter for removal and/or repositioning.

SUMMARY

The present disclosure, in its various aspects, meets an ongoing need in the field of embolization for safe, secure and accurate delivery of embolic coils within a body lumen of a patient. The present disclosure provides the ability to actively release and/or retract the embolic coil after exiting the delivery catheter.

In some aspects, the present disclosure relates to a system for delivering a vaso-occlusive coil comprising an elongate pusher member having a proximal end, a distal end and a lumen extending between the proximal and distal ends. A gripping element may be disposed at the distal end of the elongate pusher member. The gripping element may be transformable between an expanded configuration and a contracted configuration. A pushrod that includes a proximal and a distal end may be slidably disposed within the lumen of the elongate pusher member. The distal end of the pushrod may be configured to slidably engage the gripping element. A vaso-occlusive coil that includes a proximal end and distal end, may be reversibly coupled, at the proximal end of the vaso-occlusive coil, to the gripping element.

In various embodiments, which may be used in combination with the above aspects, the system further includes an elongate sheath with a proximal end, a distal end and a lumen extending between the proximal and distal ends. The elongate pusher member may be slidably disposed within the lumen of the elongate sheath.

In various embodiments, which may be used in combination with the above aspects and embodiments, the proximal end of the vaso-occlusive coil includes an attachment member having an aperture extending at least partially therethrough. The aperture of the attachment member may include at least one outwardly extending recess. The gripping element may include at least one outwardly extending projection configured to engage at least one corresponding recess of the attachment member. The gripping element may include at least one outwardly extending projection such that when the gripping member is in the expanded configuration, the at least one outwardly extending projection engages at least one corresponding recess of the attachment member, thereby securing the vaso-occlusive coil to the distal end of the elongate pusher member. When the gripping member is in the contracted configuration, on the other hand, the at least one outwardly extending projection does not substantially contact the attachment member of the vaso-occlusive coil.

In various embodiments, which may be used in combination with the above aspects and embodiments, the gripping element includes at least one outwardly extending projection configured to engage the vaso-occlusive coil. In some of these embodiments, when the gripping member is in the expanded configuration the at least one outwardly expanding projection engages at least one winding of the vaso-occlusive coil, thereby securing the vaso-occlusive coil to the distal end of the elongate pusher member. In some of these embodiments, when the gripping member is in the contracted configuration the at least one outwardly extending projection does not substantially contact the windings of the vaso-occlusive coil.

In various embodiments, which may be used in combination with the above aspects and embodiments, advancing the pushrod in the distal direction relative to the elongate pusher member urges the gripping element into the expanded configuration. Retracting the pushrod in the proximal direction relative to the elongate pusher member urges the gripping element into the contracted configuration.

In some aspects, the present disclosure relates to a system for delivering a vaso-occlusive coil comprising an elongate pusher member having a proximal end, a distal end and a lumen extending between the proximal and distal ends. The lumen at the distal end of the elongate pusher member may include a tapered portion. A retaining member that includes a proximal end and a distal end may be disposed within the lumen of the elongate pusher member and may be moveable in the proximal and distal directions relative to the elongate pusher member. The distal end of the retaining member may further include a compressible element configured to compress inwardly as the compressible element advances distally along the tapered portion of the elongate pusher member.

In various embodiments, which may be used in combination with the above aspects, the compressible element may be a compressible grommet.

In various embodiments, which may be used in combination with the above aspects and embodiments a vaso-occlusive coil that includes a proximal end and a distal end may be reversibly coupled to the retaining member by an attachment member at the proximal end of the vaso-occlusive coil.

In various embodiments, which may be used in combination with the above aspects and embodiments, the compressible element of the retaining member may include an aperture configured to receive the attachment member.

In various embodiments, which may be used in combination with the above aspects and embodiments, the system may further include an elongate sheath with a proximal end, a distal end and a lumen extending between the proximal and distal ends. The elongate pusher member may be slidably disposed within the lumen of the elongate sheath.

In various embodiments, which may be used in combination with the above aspects and embodiments, when the compressible element moves distally along the tapered portion of the elongate pusher member it applies radially inward pressure to the attachment member of the vaso-occlusive coil. When the compressible element moves proximally along the tapered portion of the elongate pusher member, on the other hand, it does not apply radially inward pressure on the attachment member of the vaso-occlusive coil.

In various embodiments, which may be used in combination with the above aspects and embodiments, distal movement of the retaining member within the lumen of the elongate sheath may be facilitated by an actuation member, including, but not limited to, a pusher member, mandrel, pressurized liquid, or pressurized gas.

In some aspects, the present disclosure relates to a system for delivering a vaso-occlusive coil comprising an elongate pusher member that includes a proximal end, a distal end and a lumen extending between the proximal and distal ends. A retaining member that includes a proximal end and a distal end may be disposed within the lumen of the elongate pusher. The retaining member may be moveable in the proximal and distal directions relative to the elongate pusher member. A vaso-occlusive coil that includes a proximal end and a distal end may be reversibly coupled, at the proximal end of the vaso-occlusive coil, to the distal end of the retaining member.

In various embodiments, which may be used in combination with the above aspects, the system may further include an elongate sheath with a proximal end, a distal end and a lumen extending between the proximal and distal ends. The elongate pusher member may be slidably disposed within the lumen of the elongate sheath. The retaining member may comprise an elongate filament that extends along the length of the elongate pusher member.

In various embodiments, which may be used in combination with the above aspects and embodiments, the elongate filament includes a distal end that is attached to the distal end of the elongate pusher member. The elongate filament may further include a plurality of windings with a shape memory transformable between a contracted configuration, in which the attachment member is engaged by the windings, and a relaxed, shape-memorized expanded configuration in which the attachment member is disengaged by the windings. Retracting the elongate filament in a proximal direction relative to the elongate pusher member transforms the plurality of windings from an expanded configuration to a contracted configuration, thereby gripping the attachment member of the vaso-occlusive coil. When in the expanded configuration, on the other hand, the plurality of windings do not substantially contact the attachment member of the vaso-occlusive coil. The proximal end of the attachment member may include an enlarged structure such that the plurality of windings do not slip off the attachment member when in the contracted configuration. The enlarged structure may have a variety of shapes including, as non-limiting examples, a cylindrical shape, a conical shape, an octagonal shape and the like.

In various embodiments, which may be used in combination with the above aspects and embodiments, the elongate filament includes a distal end with a plurality of windings having a shape memory within which the attachment member of the vaso-occlusive coil may be disposed, such that the windings are reversibly coupled to an outer surface of the attachment member. Retracting the elongate filament in a proximal direction relative to the elongate pusher member forces the plurality of windings to disengage from the surface of the attachment member, thereby releasing the vaso-occlusive coil. The distal end of the elongate pusher member may include a socket configured to receive the attachment member of the vaso-occlusive coil. The socket may include a flared portion comprising a flexible material transformable between an expanded configuration and a contracted configuration.

In various embodiments, which may be used in combination with the above aspects and embodiments, the proximal end of the vaso-occlusive coil may include an attachment member with an aperture extending therethrough. The retaining member may include an elongate filament that extends along the length of the elongate pusher member, passes through the aperture of the attachment member and extends back along the length of the elongate pusher member. Releasing one end of the elongate filament while retracting another end of the elongate filament in a proximal direction relative to the elongate pusher member removes the elongate filament from the aperture of the attachment member, thereby releasing of the vaso-occlusive coil.

In various embodiments, which may be used in combination with the above aspects and embodiments, the distal end of the pusher member may include a socket configured to receive the attachment member of the vaso-occlusive coil. The socket includes a flared portion comprising a flexible material transformable between an expanded configuration and a contracted configuration.

In yet other aspects, the present disclosure relates to a system for delivering a vaso-occlusive coil comprising an elongate pusher member having a proximal end, a distal end and a lumen extending between the proximal and distal end. The distal end of the elongate pusher member may include a flexible receptacle. A pushrod that includes a proximal end and a distal end may be slidably disposed within the lumen of the elongate pusher member. A vaso-occlusive coil that includes a proximal end and a distal end may be reversibly coupled, at the proximal end of the vaso-occlusive coil, to the flexible receptacle of the elongate pusher member.

In various embodiments, which may be used in combination with the above aspects, the system further includes an elongate sheath with a proximal end, a distal end and a lumen extending between the proximal and distal ends. The elongate pusher member may be slidably disposed within the lumen of the elongate sheath.

In various embodiments, which may be used in combination with the above aspects and embodiments, the distal end of the pushrod may be configured to abut the proximal end of the vaso-occlusive coil such that advancing the pushrod in the distal direction relative to the elongate pusher member releases the vaso-occlusive coil from the distal end of the elongate pusher member. The proximal end of the vaso-occlusive coil may include an enlarged structure (e.g., ball-tip) configured to reversibly fit within the flexible receptacle. It should be appreciated that the design of the enlarged structure may be not limited to a ball-tip, and can have a variety of geometries including, as non-limiting examples, a cylindrical shape, a conical shape, an octagonal shape and the like.

DRAWINGS

Non-limiting embodiments of the present disclosure will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure.

FIGS. 1A-D depict a spring-mediated embolic coil delivery system, in accordance with one embodiment of the present disclosure.

Figure 2A:
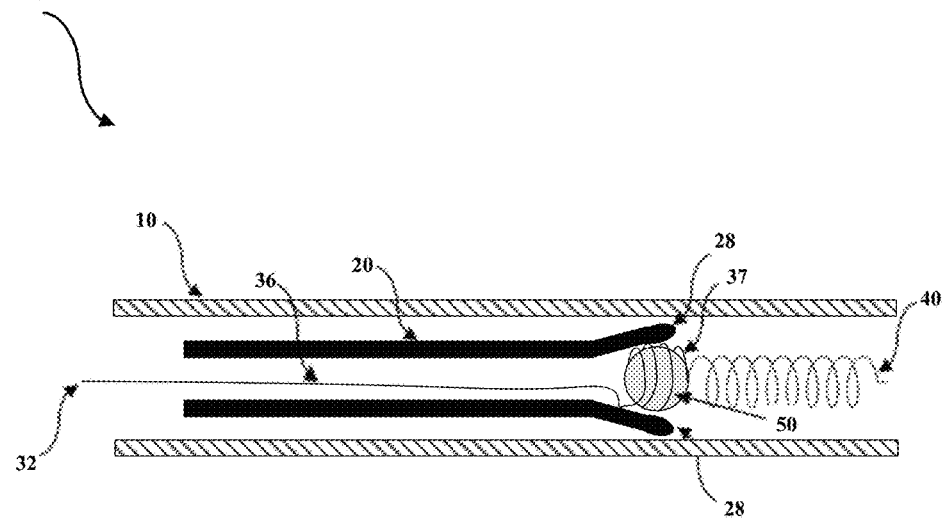
Figure 2B:
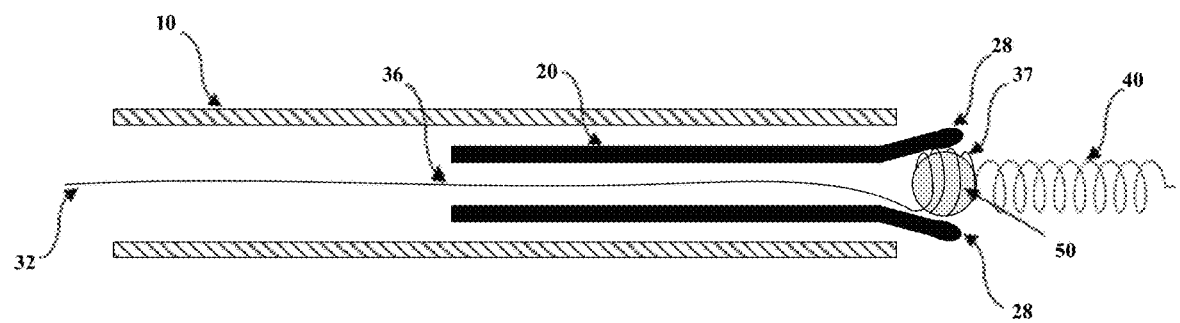
Figure 2C:
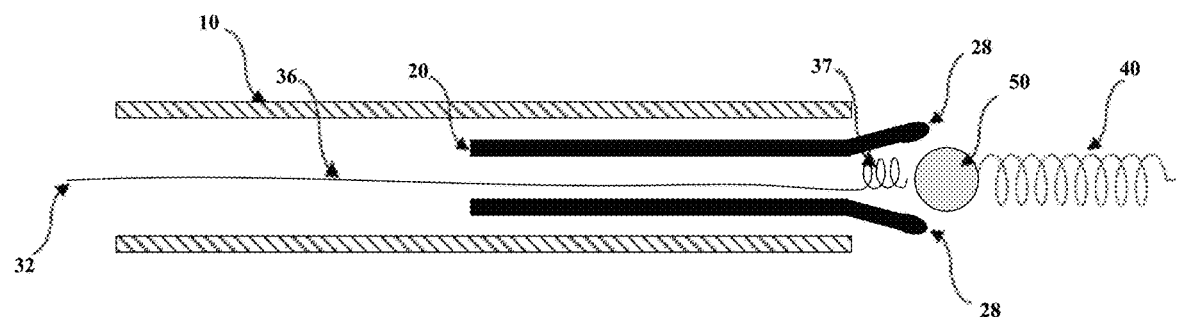

FIGS. 2A-C depict another spring-mediated embolic coil delivery system, in accordance with one embodiment of the present disclosure.

Figure 3A:
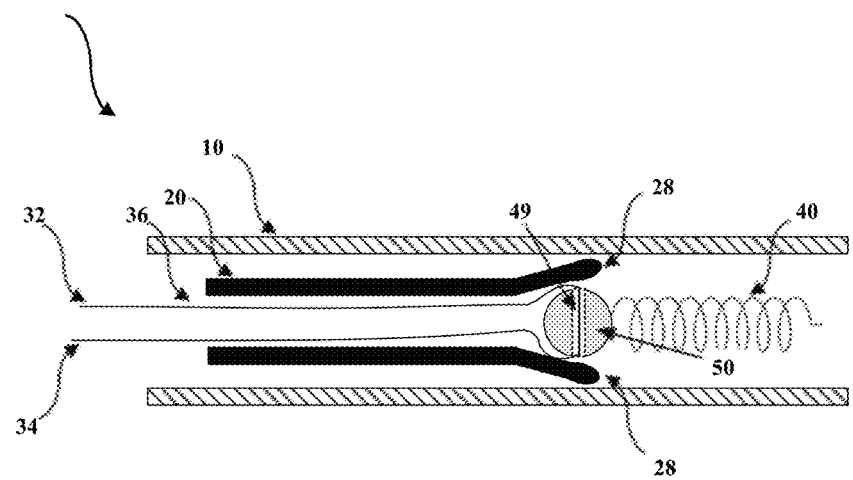
Figure 3B:
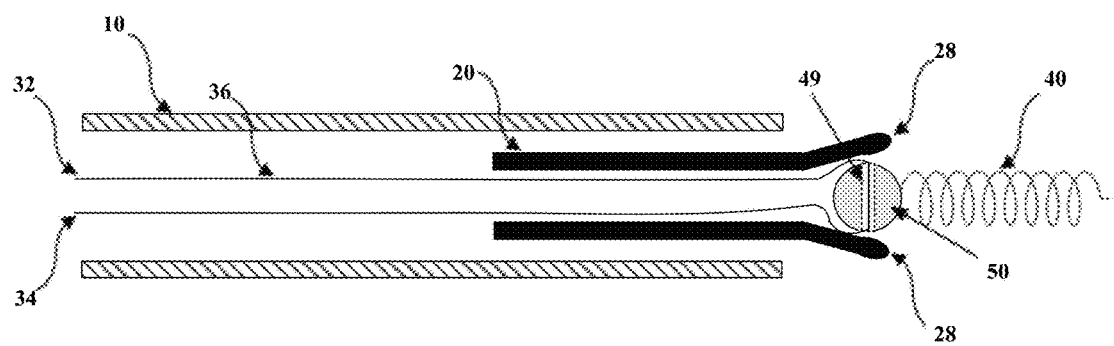
Figure 3C:
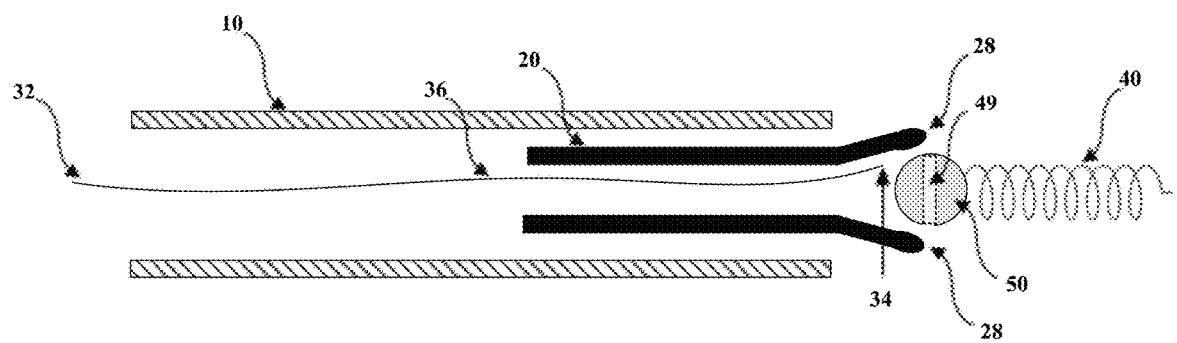

FIGS. 3A-C depict a wire-mediated embolic coil delivery system, in accordance with one embodiment of the present disclosure.

Figure 4A:
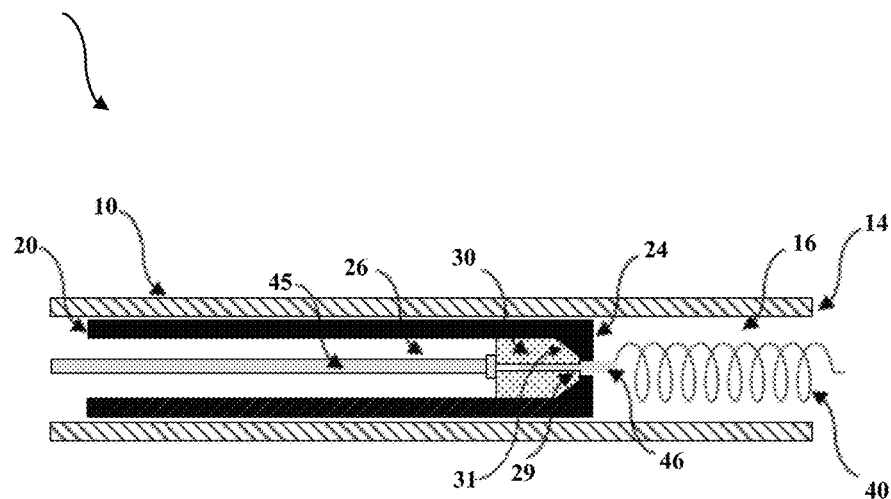
Figure 4B:
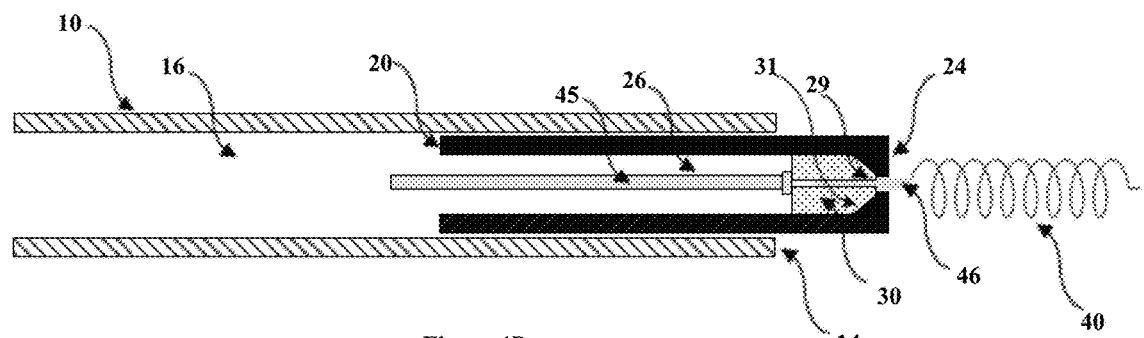
Figure 4C:
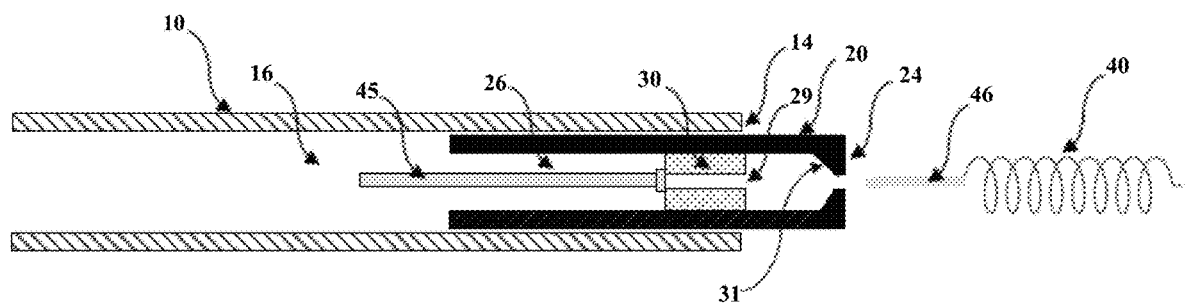

FIGS. 4A-C depict a grommet-mediated embolic coil delivery system, in accordance with one embodiment of the present disclosure.

FIGS. 5A-D depict a pushrod-mediated embolic coil delivery system, in accordance with one embodiment of the present disclosure.

FIGS. 6A-D depict an alternative view of a pushrod-mediated embolic coil delivery system, in accordance with one embodiment of the present disclosure.

Figure 7:
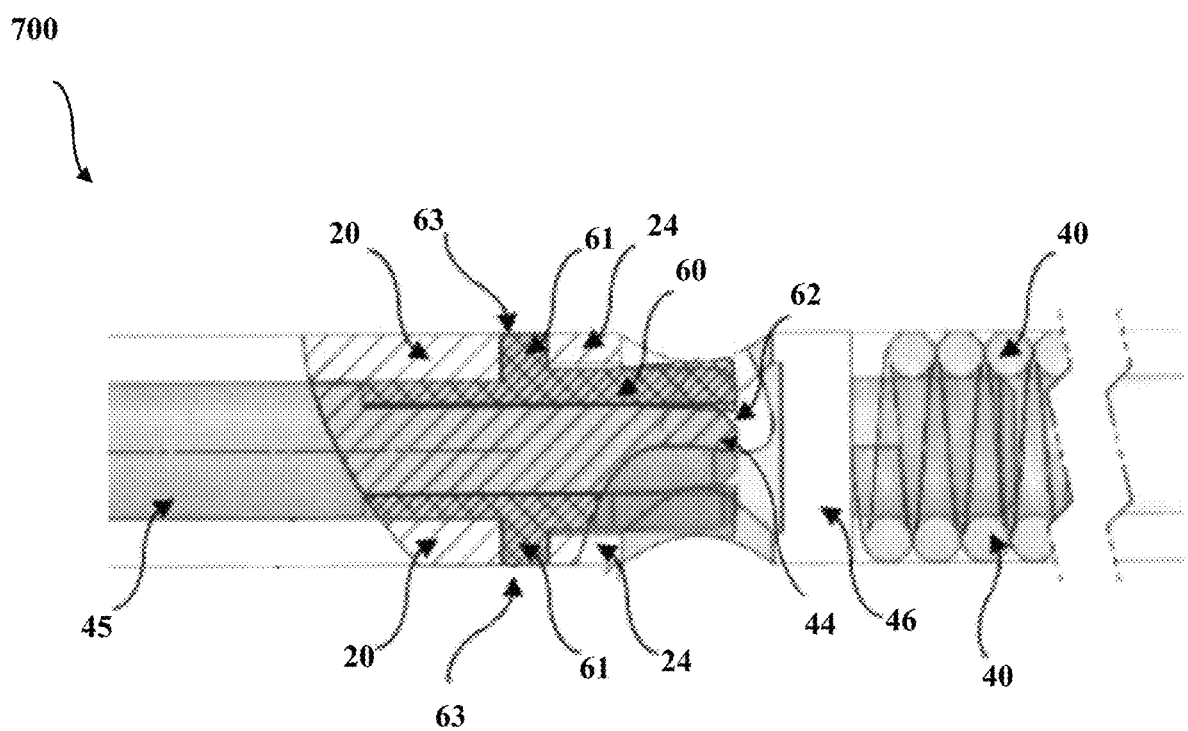

FIG. 7 depicts a compression-mediated embolic coil delivery system, in accordance with one embodiment of the present disclosure.

Figure 8A:
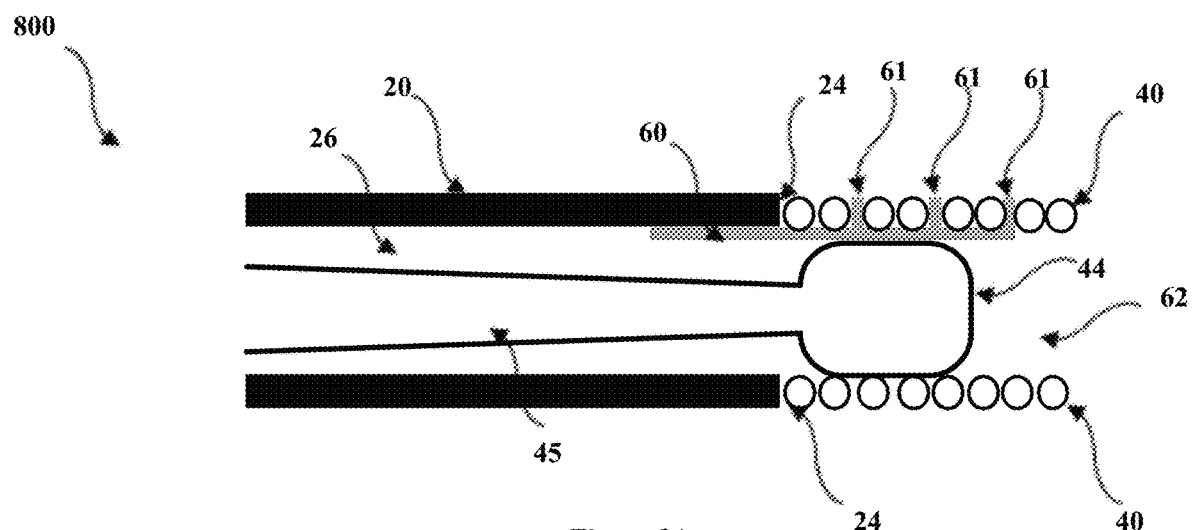
Figure 8B:
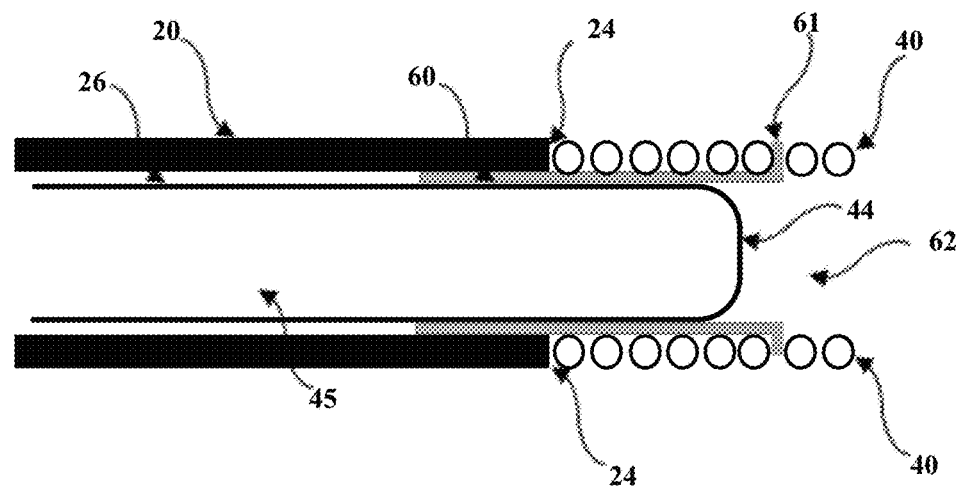
Figure 8C:
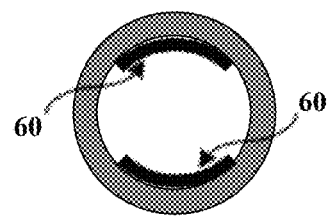

FIGS. 8A-C depict two additional compression-mediated embolic coil delivery system, in accordance with an embodiment of the present disclosure.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one or ordinary skill in the art to which the disclosure belongs. Finally, although embodiments of the present disclosure are described with specific reference to embolic coils, it should be appreciated that the scope of the disclosure may be applicable to a number of implantable devices requiring delivery to specific location(s) within a patient.

The systems and methods of the present disclosure are generally directed to systems and methods for actively releasing medical devices, including, for example, embolic coils within a body lumen of a patient. Where the medical device portion is an embolic coil, it may be formed from metals or alloys, for example, selected from platinum group metals, particularly platinum, rhodium, palladium, and rhenium, as well as tungsten, gold, silver, tantalum, and alloys of these metals including platinum/tungsten alloys and nickel-titanium alloys (nitinol) among others. These materials have significant radiopacity, and their alloys may be tailored to have a blend of flexibility and stiffness for the coil. They are also generally biologically inert.

FIGS. 1A-D generally depict a distal end of a delivery system 100 that includes an elongate sheath 10 with a proximal end (not shown), distal end 14 and lumen 16 extending therethrough. As defined herein a "sheath" is any hollow medical instrument through which an implantable device (e.g., a catheter, endoscope, etc.) may be delivered. An elongate pusher member 20 with a proximal end (not shown), distal end 24 and lumen 26 is slidably disposed within the sheath 10. The pusher member 20 may be formed, for example, from an extruded polymeric tube, tightly wound flexible coil or a slotted metallic hypotube that would be dimensionally compatible with the sheath. A vaso-occlusive coil 40 is reversibly coupled to the distal end 24 of the elongate pusher member 20 by an elongate filament 36 that extends the length of lumen 26. The distal end 34 of elongate filament 36 includes a plurality of windings 37 (e.g., a coil) having an expanded shape-memorized configuration 38 (see, e.g., FIGS. 1C-1D). Suitable shape-memorizable materials include stainless steel and nickel-titanium alloys (nitinol). The linear and coiled portions of the elongate filament may be formed of the same material or different materials. In one embodiment, the distal end of the elongate filament is attached to an inner surface of elongate pusher member 20. When in the relaxed, expanded configuration, windings 37 of filament 36 are dimensioned to receive an attachment member 46 (e.g., attachment arm) attached to the proximal end of vaso-occlusive coil 40. In one embodiment, the attachment member 46 is integrally formed with the vaso-occlusive coil. In another embodiment, the attachment member 46 is bonded to the proximal end of the vaso-occlusive coil by, for example, welding, soldering, adhesives, mechanical mating, and the like. The attachment member 46 may be formed, for example, from a material similar or identical to the vaso-occlusive coil material.

Figure 1B:
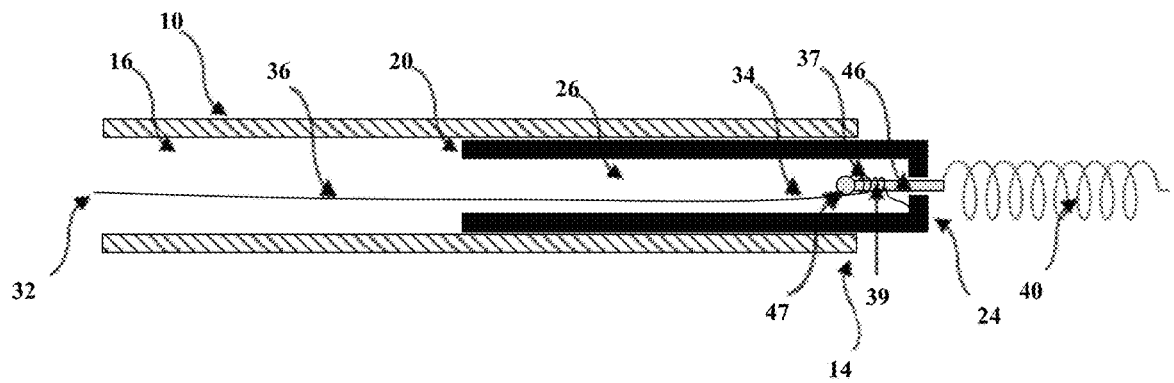
Figure 1C:
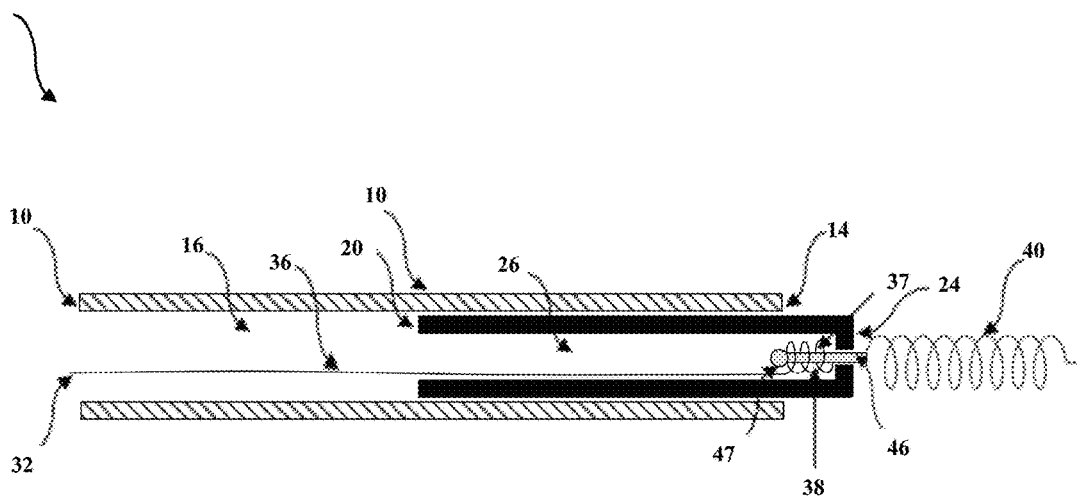
Figure 1D:
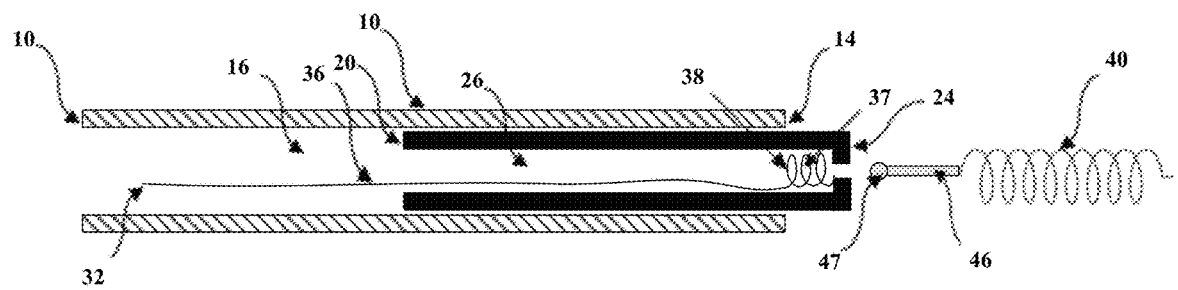

Retracting the elongate filament 36 in a proximal direction relative to the elongate pusher member 20 such that a tension force is exerted on the elongate filament while attachment member 46 is received in the windings 37, transforms the windings of filament 36 from the relaxed, expanded configuration 38 into a contracted configuration 39 (see, e.g., FIGS. 1A-1B), thereby gripping attachment member 46 to retain vaso-occlusive coil 40 on the distal end of elongate pusher member 20. In one embodiment, the proximal end of attachment member 46 optionally includes an enlarged structure 47 (e.g., ball, post etc.) to prevent filament 36 from sliding off. When the proximally directed force exerted upon proximal end 32 of elongate filament 36 is relieved (e.g., elongate filament 36 is released), the windings 37 relax and transform from the contracted configuration 39 to the expanded configuration 38. Because windings 37 do not substantially contact the attachment member 46 and/or the enlarged structure 47 when in the expanded configuration 38 (FIG. 1C), the vaso-occlusive coil is released from the distal end of elongate pusher member 20 into the patient (FIG. 1D).

In practice, and by way of example, delivery system 100 may be introduced into the patient with elongate pusher member 20 and vaso-occlusive coil 40 disposed within elongate sheath 10. The distal end of elongate filament 36 is in the contracted configuration 39 gripping attachment member 46 (FIG. 1A). Once the elongate sheath 10 is properly positioned within the patient, elongate pusher member 20 is advanced in the distal direction relative to the elongate sheath 10 such that the vaso-occlusive coil 40 is disposed outside of elongate sheath 10. Importantly, the elongate filament 36 is placed in tension (e.g., by exerting a pulling force on a proximal end of the elongate filament 36) such that windings 37 of elongate filament 36 remain in the contracted configuration 39 and the vaso-occlusive coil 40 remains attached to the distal end of elongate pusher member 20 (FIG. 1B). Vaso-occlusive coil 40 can then be repositioned as necessary by advancing or retracting elongate pusher member 20. Once the distal end of vaso-occlusive coil 40 is properly positioned within the patient, tension on the elongate filament 36 is released such that windings 37 transform to the shape-memorized expanded configuration 38 (FIG. 1C). Because attachment member 46 and enlarged structure 47 are no longer substantially engaged by the windings 37, the vaso-occlusive coil 40 is released from the distal end of elongate pusher member 20 into the patient (FIG. 1D).

FIGS. 2A-C generally depict an embodiment of the present disclosure in which the attachment member disposed on the proximal end of vaso-occlusive coil 40 includes a ball-tip 50. The distal end of elongate pusher member 20 includes a flexible socket. The ball-tip 50 may be formed, for example, from a material similar or identical to the vaso-occlusive coil material. The proximal end of the elongate pusher member 20 may be formed, for example, from an extruded polymeric tube, tightly wound flexible coil or a slotted metallic hypotube. The flexible socket may be formed, for example, of a flexible metallic or non-metallic (e.g., polymeric) material or a spring like component. While the flexible socket may be flared or non-flared, it is illustrated as a flared portion 28 in FIGS. 2A-2C. The flared portion 28 is configured to receive the outer surface of the ball-tip 50. In one embodiment, the flared portion 28 comprises a flexible material transformable between an expanded configuration and a contracted configuration (not shown). The distal end of elongate filament 36 includes a plurality of windings 37 dimensioned to reversibly engage the outer surface of ball-tip 50. The windings 37 can include a variety of configurations suitable for engaging a substantial portion of the outer surface of ball-tip 50, including (but not limited to) coils, springs and the like. For instance, the windings can include variable diameter springs in which the diameter increases and then decreases along the length of the spring (e.g., diamond-shaped springs, etc.), beneficially having a varying internal diameter approximating the dimensions the outer surface of ball-tip 50. Suitable materials for the windings 37 include, for example, stainless steel and nickel-titanium alloys (nitinol), among other possible materials. The linear portion windings 37 of the elongate filament 36 may be formed of the same material or different materials.

Pulling elongate filament 36 in a proximal direction relative to the elongate pusher member 20 with a suitable proximally directed force, urges the windings 37 of filament 36 to engage the outer surface of ball-tip 50 with a sufficient frictional force to retain the vaso-occlusive coil 40 on the flared portion 28 at the distal end of elongate pusher member 20. When the proximally directed force exerted upon the proximal end 32 of elongate filament 36 is increased beyond a threshold amount, the windings 37 of filament 36 disengage (i.e., unwrap) from the outer surface of ball-tip 50, to release the vaso-occlusive coil from the distal end of elongate pusher member 20.

In practice, and by way of example, delivery system 200 may be introduced into the patient with elongate pusher member 20 and vaso-occlusive coil 40 disposed within elongate sheath 10. The windings 37 of elongate filament 36 are disposed about, and frictionally engage, the outer surface of ball-tip 50 (FIG. 2A). Once the sheath 10 is properly positioned within the patient, elongate pusher member 20 is advanced in the distal direction relative to the elongate sheath 10 such that vaso-occlusive coil is disposed outside of elongate sheath 10. Importantly, windings 37 of elongate filament 36 remain disposed about, and frictionally engaged with, the outer surface of ball tip 50 (FIG. 2B). Vaso-occlusive coil 40 can then be repositioned as necessary by advancing or retracting elongate pusher member 20. Once the distal end of vaso-occlusive coil 40 is properly positioned within the patient, the proximally directed tensile force exerted on elongate filament 36 is gradually increased until windings 37 disengage from the outer surface of ball-tip 50, thereby releasing vaso-occlusive coil from the distal end of elongate pusher member 20 into the patient (FIG. 2C).

FIGS. 3A-C generally depict an embodiment of the present disclosure in which the attachment member disposed on the proximal end of vaso-occlusive coil 40 includes a ball-tip 50 with an aperture 49 extending therethrough. The distal end of elongate pusher member 20 includes a flexible socket. The ball-tip 50 may be formed, for example, from a material similar or identical to the vaso-occlusive coil material. The proximal end of the elongate pusher member 20 may be formed, for example, from an extruded polymeric tube or a slotted metallic hypotube. The flexible socket may be formed, for example, of a flexible metallic or non-metallic (e.g., polymeric) material or a spring like component. While the flexible socket may be flared or non-flared, it is illustrated as a flared portion 28 in FIGS. 3A-3C. The flared portion 28 is configured to receive the outer surface of the ball-tip 50. In one embodiment, the flared portion comprises a flexible material transformable between an expanded configuration and a contracted configuration (not shown). An elongate filament 36 forms a loop with proximal and distal ends 32, 34 that extends the length of the elongate pusher member 20, passes through the aperture 49 of ball-tip 50 and extends back along the length of the elongate pusher member 20. The elongate filament 36 may be formed, for example, from a flexible polymeric or metallic material such as stainless steel or nitinol.

Simultaneously retracting the proximal and distal ends 32, 34 of elongate filament 36 in a proximal direction relative to the elongate pusher member 20, or fixing one end of elongate filament 36 (e.g., proximal end 32) and retracting the other end (i.e., distal end 34), places the elongate filament 36 in tension and forces the outer surface of ball-tip 50 to engage the flared portion 28 to retain the vaso-occlusive coil 40 on the distal end of the elongate pusher member 20. The elongate filament 36 is removed from the aperture 49 of ball-tip 50 by releasing one end (e.g., proximal end 32) of the elongate filament 36 while retracting the other end (e.g., distal end 34) in the proximal direction. Once the elongate filament 36 is no longer disposed within the aperture 49 of ball-tip 50 the embolic coil is released from the distal end of elongate pusher member 20.

In practice, and by way of example, delivery system 300 may be introduced into the patient with elongate pusher member 20 and vaso-occlusive coil 40 disposed within elongate sheath 10. The elongate filament 36 extends in a loop along the length of elongate pusher member through aperture 49 of ball-tip 50 (FIG. 3A). Once the elongate sheath 10 is properly positioned within the patient, elongate pusher member 20 is advanced in the distal direction relative to the elongate sheath 10 such that vaso-occlusive coil 40 is disposed outside of elongate sheath 10. Importantly, one or both of the proximal and distal ends 32, 34 of elongate filament 36 are retracted in a proximal direction such that the vaso-occlusive coil 40 is retained on the distal end of the elongate pusher member 20 (FIG. 3B). Vaso-occlusive coil 40 can then be repositioned as necessary by advancing or retracting elongate pusher member 20. Once the distal end of vaso-occlusive coil 40 is properly positioned within the patient, the elongate filament is removed from the aperture 49 of ball-tip 50 by releasing one end of the elongate filament 36 while continuing to retract the other of the elongate filament 36 (FIG. 2C).

FIGS. 4A-C generally depict a distal end of a delivery system 400 that includes an elongate sheath 10 with a proximal end (not shown), distal end 14 and lumen 16 extending therethrough. An elongate pusher member 20 with a proximal end (not shown) and a distal end 24 and lumen 26 is slidably disposed within the elongate sheath 10. The proximal end of the elongate pusher member 20 may be formed, for example, from an extruded polymeric tube or a slotted metallic hypotube. A vaso-occlusive coil 40 is reversibly coupled to the distal end 24 of elongate pusher member 20 by a compressible retaining member 30 (e.g., grommet) slidably disposed within the lumen 26. In one embodiment, the compressible retaining member 30 is advanced proximally and distally within lumen 26 by a pushrod 45 extending along the length of elongate pusher member 20. In another embodiment, a pressurized fluid such as a liquid or compressible gas (not shown) can be used to actuate movement of the compressible retaining member 30 within lumen 26.

Compressible retaining member 30 defines an aperture 29 dimensioned to receive an attachment member 46 (e.g., attachment arm) attached to the proximal portion of vaso-occlusive coil 40. Compressible retaining member 30 may be formed, for example, from a low durometer polymer, such as an elastomeric polymer or rubber. In one embodiment, the attachment member 46 is integrally formed with the vaso-occlusive coil. In another embodiment, the attachment member 46 is bonded to the proximal end of the vaso-occlusive coil by, for example, welding, soldering adhesives and the like. The attachment member 46 may be formed, for example, from a material similar or identical to the vaso-occlusive coil material.

The lumen 26 of elongate pusher member 20 includes a tapered portion 31 at distal end 24. The tapered portion 31, may be integral to the inner diameter of the sheath or may be, for example, a separate component that is bonded or molded into the sheath. Advancing pushrod 45 in the distal direction forces the compressible retaining member to compress inwardly as it advances along the tapered portion 31. As the compressible retaining member compresses inwardly the aperture 29 collapses to compressibly engage the attachment member 46 of vaso-occlusive coil 40. The radially inward force exerted by compressible retention member 30 on attachment member 46 retains the vaso-occlusive coil 40 on the distal end of elongate pusher member 20.

In practice, and by way of example, delivery system 400 may be introduced into the patient with elongate pusher member 20 and vaso-occlusive coil 40 disposed within elongate sheath 10. Compressible retaining member 30 is disposed along tapered portion 31 such that attachment member 46 of vaso-occlusive coil 40 is compressibly engaged within aperture 29 (FIG. 4A). Once the elongate sheath 10 is properly positioned within the patient, elongate pusher member 20 is advanced in the distal direction relative to the elongate sheath 10 such that vaso-occlusive coil 40 is disposed outside of elongate sheath 10. Importantly, distally directed pressure exerted upon the compressible retaining member 30 (e.g., by pushrod 45, a pressurized fluid, or other suitable means) keeps the compressible retaining member 30 disposed along tapered portion 31 (FIG. 4B). Vaso-occlusive coil 40 can then be repositioned as necessary by advancing or retracting elongate pusher member 20. Once the distal end of vaso-occlusive coil 40 is properly positioned within the patient, the distally directed pressure exerted upon the compressible retaining member 30 is removed (e.g., by retracting the pushrod 45 in a proximal direction relative to the elongate pusher member 20; by relieving the pressure exerted by the pressurized fluid or by applying a vacuum), allowing the compressible retaining member 30 to be returned to a non-compressed state. Once the radially inward force on attachment member 46 is removed, the vaso-occlusive coil 40 is released from the distal end of elongate pusher member 20 (FIG. 4C).

FIGS. 5A-5D generally depict a distal end of a delivery system 500 that includes an elongate sheath 10 with a proximal end (not shown), distal end 14 and lumen 16 extending therethrough. An elongate pusher member 20 with a proximal end (not shown), distal end 24 and lumen 26 is slidably disposed within the elongate sheath 10. A vaso-occlusive coil 40 is reversibly coupled to the distal end 24 of the elongate pusher member 20. A ball-tip 50 is attached to the proximal end of vaso-occlusive coil 40. The ball-tip 50 may be formed, for example, from a material similar or identical to the vaso-occlusive coil material. The distal end 24 of elongate pusher member 20 includes a flexible socket 25 dimensioned to receive the outer surface of the ball-tip 50. The proximal end of the elongate pusher member 20 may be formed, for example, from an extruded polymeric tube, a tightly wound flexible coil or a slotted metallic hypotube. The flexible socket 25 may be formed, for example, of a flexible metallic or non-metallic (e.g., polymeric) material or a spring like component. A pushrod 45 with proximal end 42 and distal end 44 is slidably disposed within the lumen 26 of elongate pusher member 20. The distal end 44 of pushrod 45 is configured to contact the outer surface ball-tip 50 disposed within flexible socket 25. The flexible socket is transformable between expanded and unexpanded configurations. Advancing the pushrod 45 in the distal direction relative to the elongate pusher member 20, forces the ball-tip out of the flexible socket 25 to release the vaso-occlusive coil 40 from the distal end of the elongate pusher member 20.

In one embodiment, a pressurized fluid such as a compressible gas or liquid (not shown) can be used to actuate the release of the ball-tip 50 from the flexible socket 25.

Figure 5A:
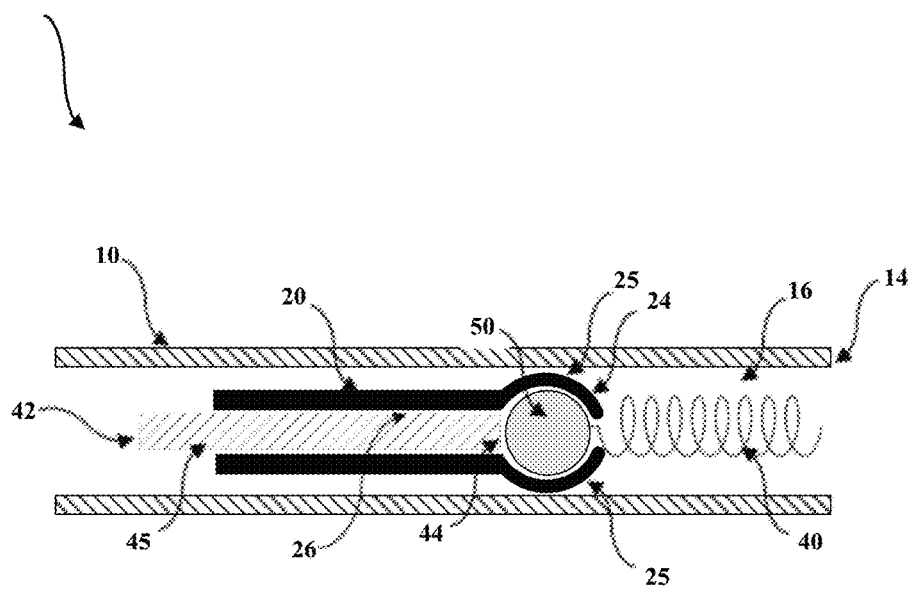
Figure 5B:
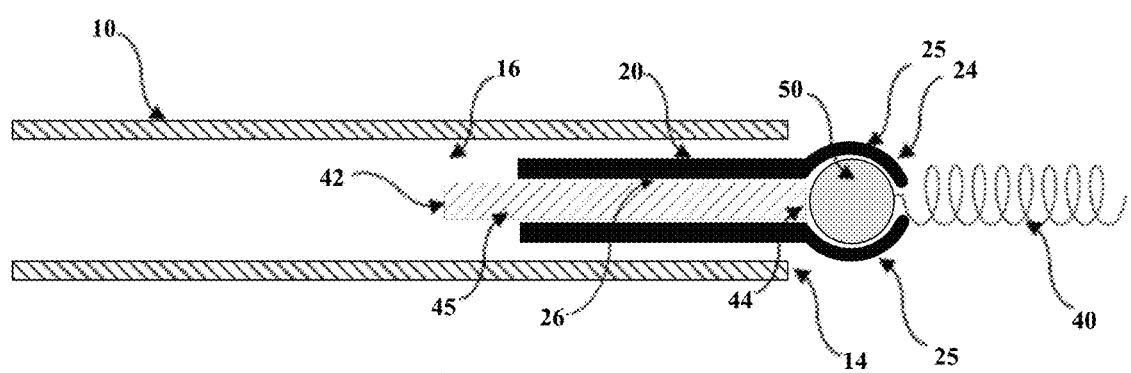
Figure 5C:
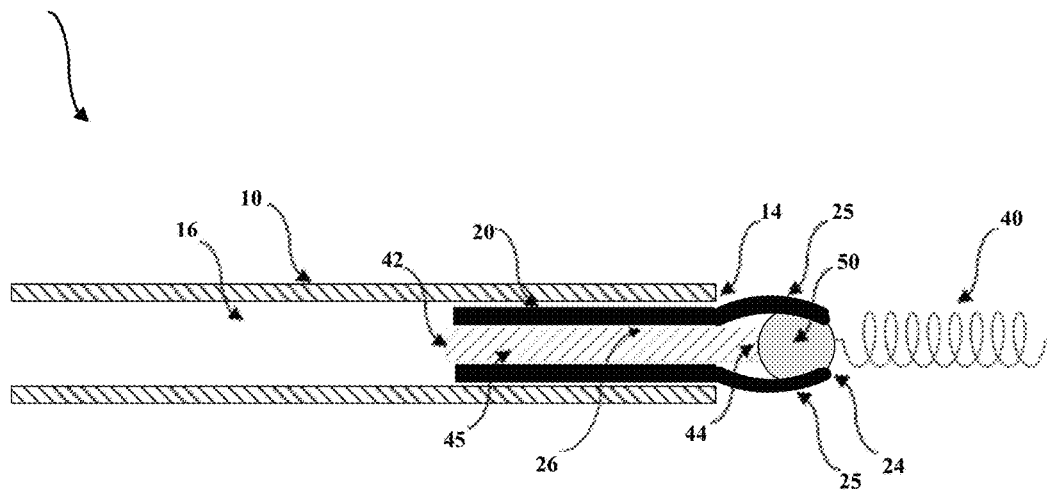
Figure 5D:
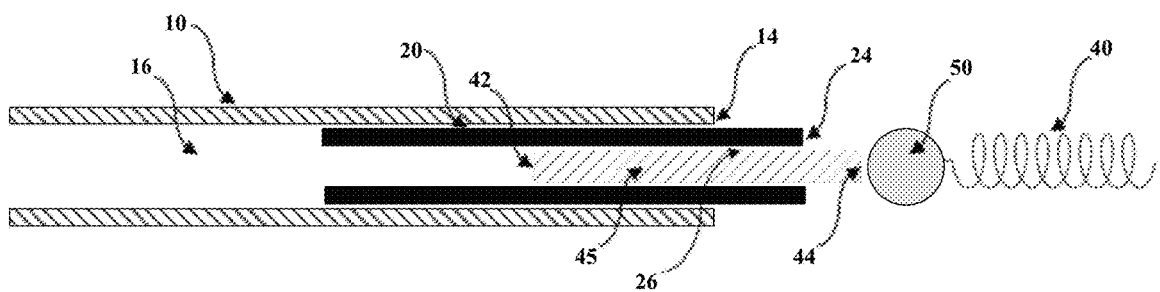

In practice, and by way of example, delivery system 500 may be introduced into the patient with elongate pusher member 20 and vaso-occlusive coil 40 disposed within elongate sheath 10. The ball-tip 50 of vaso-occlusive coil 40 is disposed within the flexible socket 25 of elongate pusher member 20 (FIG. 5A). Once the elongate sheath 10 is properly positioned within the patient, elongate pusher member 20 is advanced in the distal direction relative to the elongate sheath 10 such that vaso-occlusive coil is disposed outside of elongate sheath 10. Importantly, the distal end 44 of pushrod 45 does not substantially exert any distally directed pressure against the outer surface of ball-tip 50 (FIG. 5B). Vaso-occlusive coil 40 can then be repositioned as necessary by advancing or retracting elongate pusher member 20. Once the distal end of vaso-occlusive coil 40 is properly positioned within the patient, the pushrod 45 is advanced in the distal direction relative to the elongate pusher member 20. Flexible socket 25 deforms from an expanded to unexpanded configuration as the ball-tip 50 is advanced distally (FIG. 5C) and released into the patient (FIG. 5D). In other embodiments, the ball-tip 50 may be advanced distally from the flexible socket 25 using a pressurized fluid.

A common issue associated with delivery systems that deliver vaso-occlusive coils directly from the distal tip of the guide catheter is tendency for a proximal end of the vaso-occlusive coil to trail outside the target occlusion area into the non-occluded vasculature. The failure of the proximal end of the vaso-occlusive coil to be retained by the occlusion coil mass within the target occlusion site is referred to as a "pigtail." The likelihood of a pigtail formation tends to be higher for the last vaso-occlusive coil placed within a target occlusion area. One reason for the occurrence of pigtails is that the pusher wire (i.e., pushrod) on the distal end of the delivery system and the proximal end of the vaso-occlusive coil often form a long rigid zone that does not permit proper positioning and/or repositioning within the increasingly small occlusion area.

Figure 6A:
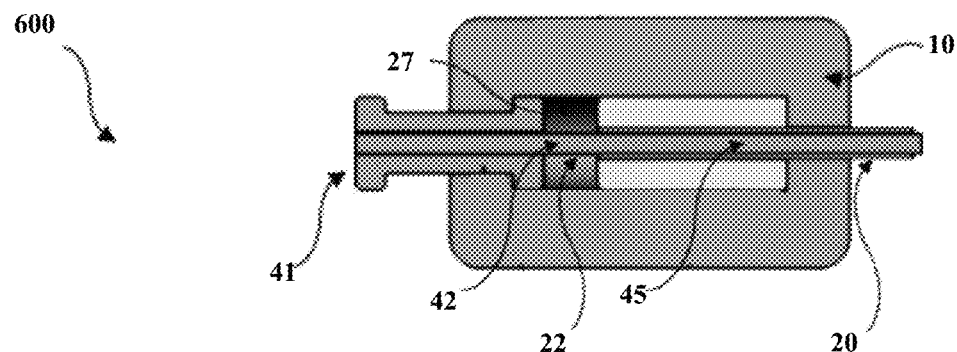
Figure 6B:
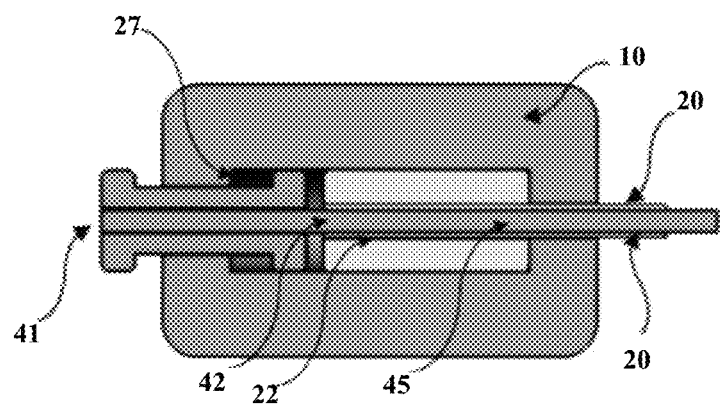
Figure 6C:
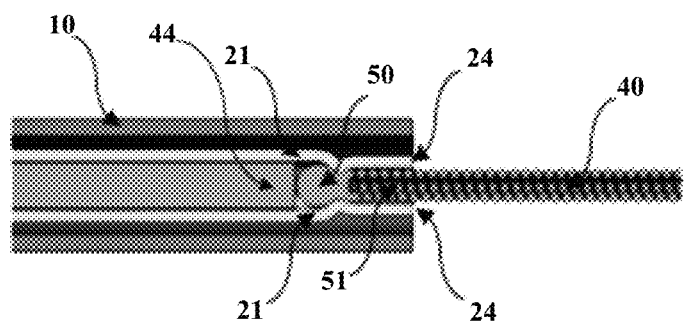
Figure 6D:
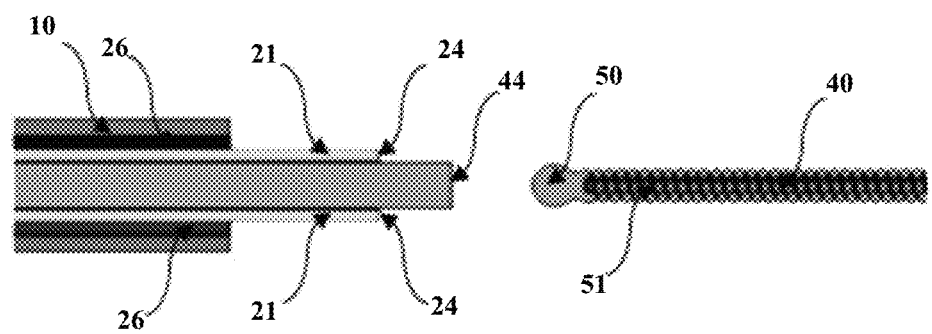

FIGS. 6A-D generally depict a delivery system 600 that is analogous to that described in FIGS. 5A-5D and includes an elongate pusher member 20 with a proximal end 22 (shown in FIGS. 6A-6B) and a distal end 24 (shown in FIGS. 6C-6D) that is slidably disposed within an elongate sheath 10 (the distal end 24 of which is shown in FIGS. 6C-6D). A vaso-occlusive coil 40 is reversibly coupled to the distal end 24 of the elongate pusher member 20. A ball-tip 50 is attached/formed to the proximal end of vaso-occlusive coil 40. The ball-tip 50 may be formed, for example, from a material similar or identical to the vaso-occlusive coil material. The distal end 24 of elongate pusher member 20 includes a flexible retaining sheath 21 dimensioned to receive the outer surface of the ball-tip 50 and, in the embodiment shown, a portion of the proximal end 51 of vaso-occlusive coil 40. A pushrod 45 with proximal end 42 and distal end 44 is slidably disposed within the lumen 26 of elongate pusher member 20. The distal end 44 of pushrod 45 is configured to contact the outer surface of ball-tip 50 disposed within flexible retaining sheath 21. The flexible retaining sheath 21 comprises an elastomeric material transformable between expanded and unexpanded configurations. Advancing the pushrod 45 in the distal direction relative to the elongate pusher member 20 forces the ball-tip out of the flexible retaining sheath 21 to release the vaso-occlusive coil 40 from the distal end of the elongate pusher member 20. As seen in FIGS. 6A-6B, the proximal end of the elongate pusher member 20 is enlarged to facilitate handling. The proximal end of the elongate pusher member 20 also includes a housing 27 within which a pushrod handle 41 is slidably disposed between a proximal position and a distal position. Moving the pushrod handle 41 from the proximal position to the distal position advances the pushrod 45 in the distal direction relative to the elongate pusher member 20 by a predetermined distance, forcing the ball-tip out of the flexible retaining sheath 21 as previously described.

In practice, and by way of example, delivery system 600 may be introduced into the patient with elongate pusher member 20 and vaso-occlusive coil 40 disposed within elongate sheath 10. The ball-tip 50 and proximal portion 51 of vaso-occlusive coil 40 are disposed within the flexible retaining sheath 21 of elongate pusher member 20 (FIG. 6C). Once the elongate sheath 10 is properly positioned within the patient, elongate pusher member 20 is advanced in the distal direction relative to the elongate sheath 10 such that the vaso-occlusive coil is disposed outside of elongate sheath 10. Importantly, the distal end 44 of pushrod 45 does not substantially exert any distally directed pressure against the outer surface of ball-tip 50. Vaso-occlusive coil 40 can then be repositioned as necessary by advancing or retracting elongate pusher member 20. Once the distal end of vaso-occlusive coil 40 is properly positioned within the target occlusion area, the pushrod handle 41 is moved from the proximal position to the distal position, advancing the pushrod 45 in the distal direction relative to the flexible retaining sheath 21 to release the vaso-occlusive coil (FIGS. 6B and 6D).

FIG. 7 generally depicts a delivery system 700 that includes an elongate pusher member 20 with a proximal end (not shown), distal end 24 and lumen (not shown). The distal end 24 of elongate pusher member 20 includes a gripping member 60 transformable between a radially expanded configuration and a radially contracted configuration. The gripping member preferably includes at least one radially outwardly extending projection 61. A vaso-occlusive coil 40 is reversibly coupled to the distal end 24 of the elongate pusher member 20. An attachment member 46 including a lumen 62 extending at least partially therethrough is attached to the proximal end of vaso-occlusive coil 40. The lumen 62 of attachment member 46 is dimensioned to receive gripping member 60 when in the contracted configuration. The lumen 62 of attachment member 46 further includes at least one outwardly extending recess 63 dimensioned to receive the outwardly extending projection 61 of gripping member 60 when in the expanded configuration. A pushrod 45 (i.e., stylet) with proximal end (not shown) and distal end 44 is slidably disposed within the lumen 26 of elongate pusher member 20. The distal end 44 of pushrod 45 is configured to slidably engage the gripping member 60. Advancing pushrod 45 in the distal direction along the surface of gripping member 60 creates an interference fit with the gripping member 60, pushing the projections 61 outward to create a compression fit between the projection 61 and the attachment member 46. Retracting the pushrod 45 in the proximal direction relative to the gripping member 60 allows the gripping member 60 to return to the contracted configuration releasing the vaso-occlusive coil 40. When in the expanded configuration, the outwardly extending projection 61 on gripping member 60 is received by outwardly extending recess 63 of attachment member 46 to interlock the vaso-occlusive coil to the distal end of elongate pusher member 20.

In practice, and by way of example, delivery system 700 may be introduced into the patient with elongate pusher member 20 and vaso-occlusive coil 40 disposed within an elongate sheath (not shown). The pushrod 45 is disposed along/over the surface of gripping element 60 such that the outwardly extending projection 61 interlocks with the outwardly extending recess 63, thereby securing the vaso-occlusive coil to the distal end of elongate pusher member 20. Once the sheath is properly positioned within the patient, elongate pusher member 20 is advanced in the distal direction relative to the elongate sheath such that vaso-occlusive coil is disposed outside of elongate sheath. Vaso-occlusive coil 40 can then be repositioned as necessary by advancing or retracting elongate pusher member 20. Once the distal end of vaso-occlusive coil 40 is properly positioned within the target occlusion area, the pushrod 45 is retracted in the proximal direction relative to the elongate pusher member 20 such that gripping member 60 transforms to the contracted configuration to release the vaso-occlusive coil 40 into the patient.

FIGS. 8A-C generally depict a delivery system 800 that includes an elongate pusher member 20 with a proximal end (not shown), distal end 24 and lumen 26. The distal end 24 of elongate pusher member 20 includes a gripping member 60 transformable between a radially expanded configuration and a radially contracted configuration. The gripping member preferably includes at least one outwardly extending projection 61. In FIG. 8A, a single gripping member 60 with three outwardly extending projections 61 is shown. In FIG. 8B, two gripping members 60 with one outwardly extending projection 61 are shown. FIG. 8C is an end view of FIG. 8B. A vaso-occlusive coil 40 is reversibly coupled to the distal end 24 of the elongate pusher member 20. The vaso-occlusive coil includes a plurality of windings that define a lumen 26 therethrough. The space between the windings of the vaso-occlusive coil are dimensioned to receive outwardly extending projection 61 when gripping member 60 is in the radially expanded configuration. A pushrod 45 (i.e., stylet) with proximal end (not shown) and distal end 44 is slidably disposed within the lumen 26 of elongate pusher member 20. The distal end 44 of pushrod 45 is configured to slidably engage the gripping member 60. Advancing pushrod 45 in the distal direction along the surface of gripping member 60 urges the gripping member 60 into the expanded configuration. Similarly, retracting pushrod 45 in the proximal direction off of the surface of gripping member 60 allows the gripping member to return to the contracted configuration. When in the expanded configuration the outwardly extending projection 61 on gripping member 60 engage (i.e., fit between) the space between the windings of the vaso-occlusive coil 40 to interlock the vaso-occlusive coil to the distal end of elongate pusher member 20.

In practice, and by way of example, delivery system 800 may be introduced into the patient with elongate pusher member 20 and vaso-occlusive coil 40 disposed within elongate sheath (not shown). The pushrod 45 is disposed along/over the surface of gripping element 60 such that the outwardly extending projection 61 interlocks with a winding of the vaso-occlusive coil 40, thereby securing the vaso-occlusive coil to the distal end of elongate pusher member 20. Once the sheath is properly positioned within the patient, elongate pusher member 20 is advanced in the distal direction relative to the elongate sheath such that vaso-occlusive coil is disposed outside of elongate sheath. Vaso-occlusive coil 40 can then be repositioned as necessary by advancing or retracting elongate pusher member 20. Once the distal end of vaso-occlusive coil 40 is properly positioned within the target occlusion area, the pushrod 45 is retracted in the proximal direction relative to the elongate pusher member 20 such that gripping member 60 transforms to the contracted configuration to release the vaso-occlusive coil 40 into the patient.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for delivering a vaso-occlusive coil, comprising:
   an elongate pusher member having a proximal end, a distal end and a lumen extending between the proximal and distal ends;
   a gripping element disposed at the distal end of the elongate pusher member, wherein the gripping element is configured to move between an expanded configuration and a contracted configuration, and wherein the gripping element includes a first plurality of projections extending outwardly in substantially the same radial direction;
   a pushrod having a proximal end and a distal end, the pushrod slidably disposed within the lumen of the elongate pusher member, wherein the distal end of the pushrod is configured to slidably engage the gripping element; and
   a vaso-occlusive coil having a proximal end and a distal end, wherein the first plurality of projections each engage a winding of the vaso-occlusive coil when the gripping element is in the expanded configuration to reversibly couple the vaso-occlusive coil to the gripping element.

2. The system of claim 1, further comprising an elongate sheath having a proximal end, a distal end and a lumen extending between the proximal and distal ends, wherein the elongate pusher member is slidably disposed within the lumen of the elongate sheath.

3. The system of claim 1, wherein the first plurality of outwardly extending projections do not substantially contact the winding of the vaso-occlusive coil when the gripping member is in the contracted configuration.

4. The system of claim 1, wherein advancing the pushrod in a distal direction relative to the elongate pusher member moves the gripping element to the expanded configuration.

5. The system of claim 1, wherein retracting the pushrod in a proximal direction relative to the elongate pusher member moves the gripping element to the contracted configuration.

6. The system of claim 1, wherein the gripping element further comprises a second plurality of radial projections extending outwardly in a substantially opposite radial direction of the first plurality of projections.

7. The system of claim 6, wherein the second plurality of radial projections comprises a number of projections equal to a number of the first plurality of radial projections and wherein the first plurality of projections and the second plurality of projections engage the same windings of the vaso-occlusive coil.

8. The system of claim 1, wherein a proximal portion of the gripping element is attached to the elongate pusher member.

9. The system of claim 1, wherein the first plurality of projections comprises three projections.

10. A system for delivering a vaso-occlusive coil, comprising:
    an elongate pusher member having a proximal end, a distal end and a lumen extending between the proximal and distal ends;
    a gripping element disposed at the distal end of the elongate pusher member, wherein the gripping element is configured to move between an expanded configuration and a contracted configuration, and wherein the gripping element includes a first plurality of projections extending outwardly in substantially the same radial direction;

a pushrod having a proximal end and a distal end, the pushrod slidably disposed within the lumen of the elongate pusher member, wherein the distal end of the pushrod is configured to slidably engage the gripping element; and a vaso-occlusive coil having a proximal end and a distal end, wherein the first plurality of projections each fit between windings of the vaso-occlusive coil when the gripping element is in the expanded configuration to reversibly couple the vaso-occlusive coil to the gripping element.

11. The system of claim 10, wherein the first plurality of outwardly extending projections do not substantially contact the winding of the vaso-occlusive coil when the gripping member is in the contracted configuration.

12. The system of claim 10, wherein advancing the pushrod in a distal direction relative to the elongate pusher member moves the gripping element to the expanded configuration.

13. The system of claim 10, wherein retracting the pushrod in a proximal direction relative to the elongate pusher member moves the gripping element to the contracted configuration.

14. The system of claim 10, wherein the gripping element further comprises a second plurality of radial projections extending outwardly in a substantially opposite radial direction of the first plurality of projections.

15. The system of claim 10, wherein a proximal portion of the gripping element is attached to the elongate pusher member.

16. A system for delivering a vaso-occlusive coil, comprising:

an elongate pusher member having a proximal end, a distal end and a lumen extending between the proximal and distal ends;

a gripping element disposed at the distal end of the elongate pusher member, wherein the gripping element is configured to move between an expanded configuration and a contracted configuration, and wherein the gripping element includes a first plurality of projections extending outwardly in substantially the same radial direction;

a pushrod having a proximal end and a distal end, the pushrod slidably disposed within the lumen of the elongate pusher member, wherein the distal end of the pushrod is configured to slidably engage the gripping element; and a vaso-occlusive coil having a proximal end and a distal end, wherein the first plurality of projections each extend between adjacent windings of the vaso-occlusive coil when the gripping element is in the expanded configuration to reversibly couple the vaso-occlusive coil to the gripping element.

17. The system of claim 16, wherein the first plurality of outwardly extending projections do not substantially contact the winding of the vaso-occlusive coil when the gripping member is in the contracted configuration.

18. The system of claim 16, wherein the first plurality of outwardly extending projections do not substantially contact the winding of the vaso-occlusive coil when the gripping member is in the contracted configuration.

19. The system of claim 16, wherein advancing the pushrod in a distal direction relative to the elongate pusher member moves the gripping element to the expanded configuration.

20. The system of claim 16, wherein retracting the pushrod in a proximal direction relative to the elongate pusher member moves the gripping element to the contracted configuration.

* * * * *